(12) United States Patent
Yang

(10) Patent No.: US 12,402,815 B2
(45) Date of Patent: Sep. 2, 2025

(54) INTEGRATED ANALYTE DETECTION SYSTEM

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 901 days.

(21) Appl. No.: 17/613,082

(22) PCT Filed: Feb. 20, 2020

(86) PCT No.: PCT/CN2020/075966
§ 371 (c)(1),
(2) Date: Nov. 22, 2021

(87) PCT Pub. No.: WO2021/031541
PCT Pub. Date: Feb. 25, 2021

(65) Prior Publication Data
US 2022/0234039 A1 Jul. 28, 2022

(30) Foreign Application Priority Data
Aug. 19, 2019 (WO) ............... PCT/CN2019/101271

(51) Int. Cl.
*B01L 3/00* (2006.01)
*A61B 5/00* (2006.01)
(Continued)

(52) U.S. Cl.
CPC ........ *A61B 5/14532* (2013.01); *A61B 5/0002* (2013.01); *A61B 5/002* (2013.01);
(Continued)

(58) Field of Classification Search
CPC ... A61B 5/14532; A61B 5/0002; A61B 5/002; A61B 5/14503; A61B 5/1451;
(Continued)

(56) References Cited

U.S. PATENT DOCUMENTS

2006/0020186 A1  1/2006 Brister et al.
2010/0217093 A1  8/2010 Ko et al.

FOREIGN PATENT DOCUMENTS

CN  107361775  11/2017
CN  109475332  3/2019
(Continued)

OTHER PUBLICATIONS

"International Search Report (Form PCT/ISA/210) of PCT/CN2020/075966," mailed on Jun. 10, 2020, pp. 1-4.

*Primary Examiner* — Jill A Warden
*Assistant Examiner* — Michael Stanley Gzybowski
(74) *Attorney, Agent, or Firm* — JCIP GLOBAL INC.

(57) ABSTRACT

The invention discloses a highly integrated analyte detection system, including: a bottom case; a sensor structure, the sensor structure includes a sensor and a sensor base, the sensor includes a signal output end and a detection end, and at least two first electrical connection areas insulated from each other are provided on the surface of the signal output end; and a transmitter, the transmitter and the bottom case are fastened with each other, and the transmitter is provided with second electrical connection areas, which are insulated from each other, corresponding to the first electrical connection areas, each second electrical connection area is electrically connected to the corresponding first electrical connection area. Such a design reduces the height of the sensor structure, making the overall structure of the detection system more compact, as a result, reducing the volume and enhancing the user experience.

8 Claims, 9 Drawing Sheets

(51) Int. Cl.
    *A61B 5/145*     (2006.01)
    *A61B 5/1468*     (2006.01)
    *A61B 5/1473*     (2006.01)
    *A61M 5/158*     (2006.01)
    *A61M 5/172*     (2006.01)
    *H01M 50/247*     (2021.01)
    *H01M 50/271*     (2021.01)

(52) U.S. Cl.
    CPC ........ *A61B 5/14503* (2013.01); *A61B 5/1451* (2013.01); *A61B 5/14546* (2013.01); *A61B 5/1468* (2013.01); *A61B 5/1473* (2013.01); *A61B 5/683* (2013.01); *A61B 5/6838* (2013.01); *A61B 5/6848* (2013.01); *A61B 5/6849* (2013.01); *A61M 5/158* (2013.01); *A61M 5/1723* (2013.01); *B01L 3/502715* (2013.01); *B01L 3/505* (2013.01); *B01L 3/508* (2013.01); *H01M 50/247* (2021.01); *H01M 50/271* (2021.01); *A61B 2560/0214* (2013.01); *A61B 2560/045* (2013.01); *A61B 2560/0462* (2013.01); *A61B 2560/0468* (2013.01); *A61B 2562/16* (2013.01); *A61B 2562/225* (2013.01); *A61B 2562/227* (2013.01); *A61M 2205/0216* (2013.01); *A61M 2205/0233* (2013.01); *B01L 2200/0689* (2013.01); *B01L 2300/023* (2013.01); *B01L 2300/0609* (2013.01); *B01L 2300/0645* (2013.01); *B01L 2300/0663* (2013.01); *B01L 2300/123* (2013.01); *B01L 2400/0677* (2013.01)

(58) Field of Classification Search
    CPC . A61B 5/14546; A61B 5/1468; A61B 5/1473; A61B 5/683; A61B 5/6838; A61B 5/6848; A61B 5/6849; A61B 2560/0214; A61B 2560/045; A61B 2560/0462; A61B 2560/0468; A61B 2562/16; A61B 2562/225; A61B 2562/227; H01M 50/247; H01M 50/271; B01L 3/502715; B01L 3/505; B01L 3/508; B01L 2200/0689; B01L 2300/023; B01L 2300/0609; B01L 2300/0645; B01L 2300/0663; B01L 2300/123; B01L 2400/0677

See application file for complete search history.

(56) References Cited

FOREIGN PATENT DOCUMENTS

| | | | |
|---|---|---|---|
| CN | 109998555 | | 7/2019 |
| CN | 110584676 | A * | 12/2019 |
| WO | 2010091005 | | 8/2010 |
| WO | 2017116915 | | 7/2017 |
| WO | 2017176797 | | 10/2017 |
| WO | 2018027940 | | 2/2018 |

* cited by examiner

INTEGRATED ANALYTE DETECTION SYSTEM

CROSS-REFERENCE TO RELATED APPLICATION

This application is a 371 of international application of PCT application serial no. PCT/CN2020/075966, filed on Feb. 20, 2020, which claims the priority benefits of PCT application serial no. PCT/CN2019/101271, filed on Aug. 19, 2019. The entirety of each of the above-mentioned patent applications is hereby incorporated by reference herein and made a part of this specification.

TECHNICAL FIELD

The present invention mainly relates to the field of medical device, and in particular, to a highly integrated analyte detection system.

BACKGROUND

The pancreas in a normal person can automatically monitor the amount of glucose in the blood and automatically secrete the required dosage of insulin/glucagon. However, for diabetic patients, the function of the pancreas is abnormal, and the pancreas cannot normally secrete required dosage of insulin. Therefore, diabetes is a metabolic disease caused by abnormal pancreatic function, which is also a lifelong disease. At present, medical technology cannot cure diabetes, and it can only control the occurrence and development of diabetes and its complications by stabilizing blood glucose.

Patients with diabetes need to check their blood glucose before injecting insulin into the body. At present, most of the detection methods can continuously detect blood glucose, and send the blood glucose data to the remote device in real time for the user to view. This detection method is called Continuous Glucose Monitoring (CGM) method. The method requires the sensing device to be attached to the surface of the patients' skin, and the probe carried by the device is inserted into the subcutaneous tissue fluid for testing.

However, the current detection device is not compact, resulting in thicker overall and larger volume, affecting the user's dressing, stretching, exercise and other daily activities, which can seriously worsen user experience. Also, detection can be easily interrupted with such a sensing device because a bulky device can get bumped or caught easily, which may lead to data loss and pose a potential safety hazard to the user.

Accordingly, there is a need in the state of the art for a detection device that has compact internal structure and small volume.

BRIEF SUMMARY OF THE INVENTION

The embodiment of the invention discloses a highly integrated analyte detection system. The sensor has a shape of a polyline or an arc, which reduces the height of the sensor structure, making the overall structure of the detection system more compact, further, as a result, reducing the volume and enhancing the user experience.

The invention discloses a highly integrated analyte detection system, including: a bottom case; a sensor structure, the sensor structure and the bottom case are fastened with each other, the sensor structure includes a sensor and a sensor base, the sensor includes a signal output end and a detection end, the output end has a shape of a polyline or an arc toward the top surface of the sensor base, and at least two first electrical connection areas insulated from each other are provided on the surface of the signal output end; and a transmitter, the transmitter and the bottom case are fastened with each other, and the transmitter is provided with the second electrical connection areas which are insulated from each other and correspond to the first electrical connection areas, each second electrical connection area is electrically connected to each corresponding first electrical connection area.

According to one aspect of the present invention, the second electrical connection areas are metal contacts.

According to one aspect of the present invention, the signal output end is a planar structure and is laid on the top of the sensor base.

According to one aspect of the present invention, it further includes a sealing member, the sealing member is arranged around the position where the signal output end is electrically connected with the electrical connection area.

According to one aspect of the present invention, a mounting hole is provided on the bottom board of the bottom case, the first fastener part is provided at the edge of the mounting hole, and the second fastener part is provided at the edge of the sensor base, the contour shapes of the edge of the sensor base and that of the mounting hole match each other, the first fastener part and the second fastener part are fastened with each other, the edge of the mounting hole and the edge of the sensor base are interlocked, and the sensor base is installed in the mounting hole.

According to one aspect of the present invention, it further includes the first elastic conductive member disposed between the first electrical connection areas and the second electrical connection areas.

According to one aspect of the present invention, the first elastic conductive member includes conductive areas and insulation areas, and the insulation area is spaced between two adjacent conductive areas, the conductive areas and the insulation areas expand across the first elastic conductive member in a vertical direction, respectively.

According to one aspect of the present invention, the conductive areas and the insulation areas are separated from each other, the first electrical connection areas are electrically connected with the corresponding second electrical connection areas through the conductive areas, and the insulation area is disposed between two adjacent first electrical connection areas or two adjacent second electrical connection areas.

According to one aspect of the present invention, the transmitter is provided with at least two third electrical connection areas, and the second elastic conductive member is disposed between the third electrical connection areas and the sensor base, after electrical connecting with the second elastic conductive member, the different third electrical connection areas are connected.

Compared with the prior art, the technical solution of the present invention has the following advantages:

In the highly integrated analyte detection system disclosed in the present invention, the signal output end has a shape of a polyline or an arc toward the top surface of the sensor base, which can reduce the height of the sensor structure, so that no extra space is required in the transmitter to accommodate the structure protruding from the bottom board of the bottom case, making the overall structure of the detection system more compact, thinner and smaller and greatly enhancing the user experience.

Furthermore, the second electrical connection areas are metal contacts. Metal contacts can reduce the electrical connection area and the volume of the analyte detection system.

Furthermore, the signal output end is a planar structure and is laid on the top of the sensor base. Because the thickness of the sensor is extremely thin (at micron level), the height of the sensor structure does not increase when the signal output end is laid on the top of the sensor base, which no extra space is required to accommodates the signal output end protruding from bottom base, ultimately reducing the thickness of the transmitter and the volume of the detection system.

Furthermore, a mounting hole is provided on the bottom board of the bottom case, the first fastener part is provided at the edge of the mounting hole, and the second fastener part is provided at the edge of the sensor base. Setting the fastener part at the edge can finally reduce the height of the fastening position, making the internal structure more compact. In addition, the contour shape of the edge of the sensor base matches that of the mounting hole, the first fastener part and the second fastener part are fastened with each other, and the edge of the mounting hole and the edge of the sensor base are interlocked with each other. The interlocked edge of the mounting hole and the sensor base makes the sensor structure entirely embedded in the mounting hole, which further reduces the height of the top of the sensor structure and is conducive to reduce the volume of the detection system.

Furthermore, the highly integrated analyte detection system further includes the first elastic conductive member disposed between the first electrical connection areas and the second electrical connection areas. The elastic conductive member can make a better electrical connect between the first electrical connection areas and the second electrical connection areas.

Furthermore, the conductive areas and the insulation areas of the first elastic conductive member are separated from each other. The first electrical connection areas is electrically connected to the corresponding second electrical connection areas through the conductive areas, and the insulation area is set between the adjacent first electrical connection areas or the adjacent second electrical connection areas. Such a design ensures that the first elastic conductive member 114 can only conduct electricity in the vertical direction without conducting electricity in the horizontal direction, achieving electrical conductivity of the first elastic conductive member 114 and also making the internal structure of the detection system more compact.

BRIEF DESCRIPTION OF THE DRAWINGS

FIG. 4d is a schematic cross-sectional structural view of the first elastic conductive member obtained along a section line B-B' in FIG. 4a;

FIG. 5c is a longitudinal sectional structural view of the highly integrated analyte detection system of FIG. 5a.

DETAILED DESCRIPTION

Figure 1:
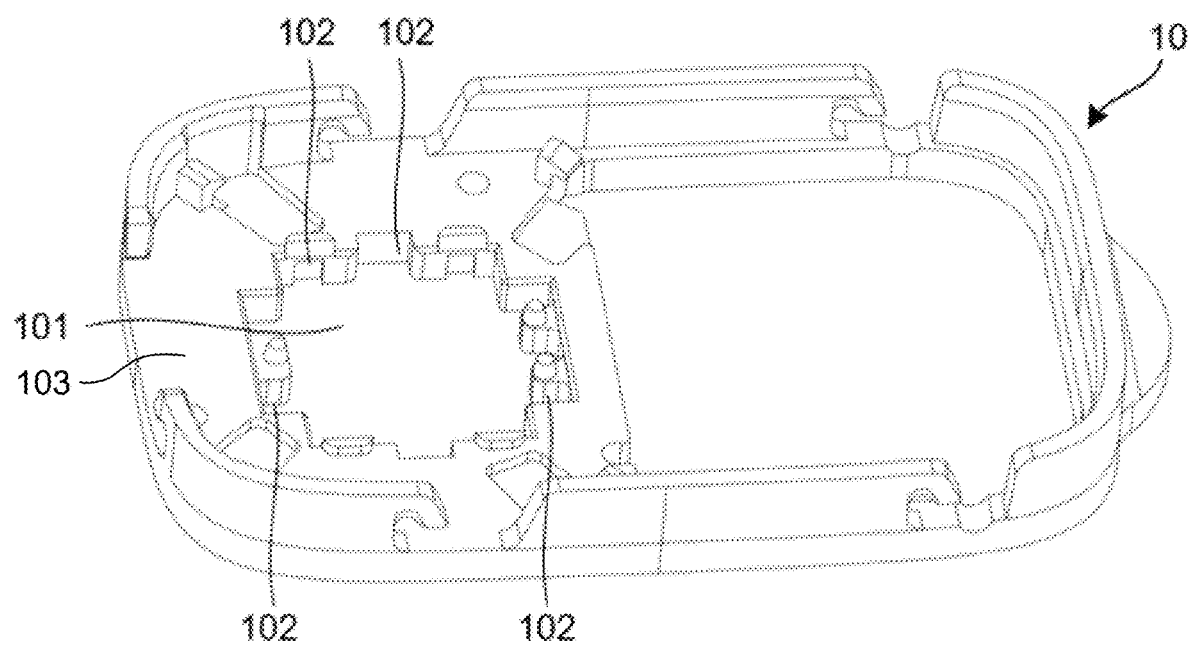
FIG. 1 is a schematic perspective view of a bottom case according to an embodiment of the present invention.

As mentioned above, the prior art body fluid parameter detection device has a larger volume and is easy to get caught while being worn on the skin surface, which leads to poor user experiences and brings inconvenience to the patient's life.

After research, it is found that the reason for the above problem is that the height of the sensor structure protruding from the inner bottom surface of the bottom case in the prior detection device is large. Extra space is required along the thickness direction of the transmitter to accommodate the foresaid protruding portion, increasing the thickness of the transmitter.

In order to solve this problem, the present invention provides a highly integrated analyte detection device. The signal output end has a shape of a polyline or an arc toward the top surface of the sensor base, which can reduce the height of the sensor structure, so that no extra space is required in the transmitter to accommodate the structure protruding from the bottom board of the bottom case, making the overall structure of the detection system more compact, thinner and smaller and greatly enhancing the user experience.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, the width, the length or the distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in following description of the drawings.

FIG. 1 is a schematic perspective view of a bottom case 10 according to an embodiment of the present invention.

The bottom case 10 is used for mounting the sensor structure and the transmitter. In the embodiment of the present invention, the bottom board 103 of the bottom case 10 is provided with a mounting hole 101 for mounting the sensor structure, while the fastener structure for fixing the transmitter is designed on the side wall of the bottom case 10.

In the embodiment of the present invention, a first fastener part 102 is provided at the edge of the mounting hole 101. Here, being provided at the "edge" means that the top of the first fastener part 102 is not higher than or slightly higher than the inner bottom surface of the bottom case 10.

The embodiment of the present invention does not specifically limit the shape and type of the first fastener part 102 and the shape of the mounting hole 101, as long as the conditions for mounting the sensor structure can be satisfied.

Figure 2A:
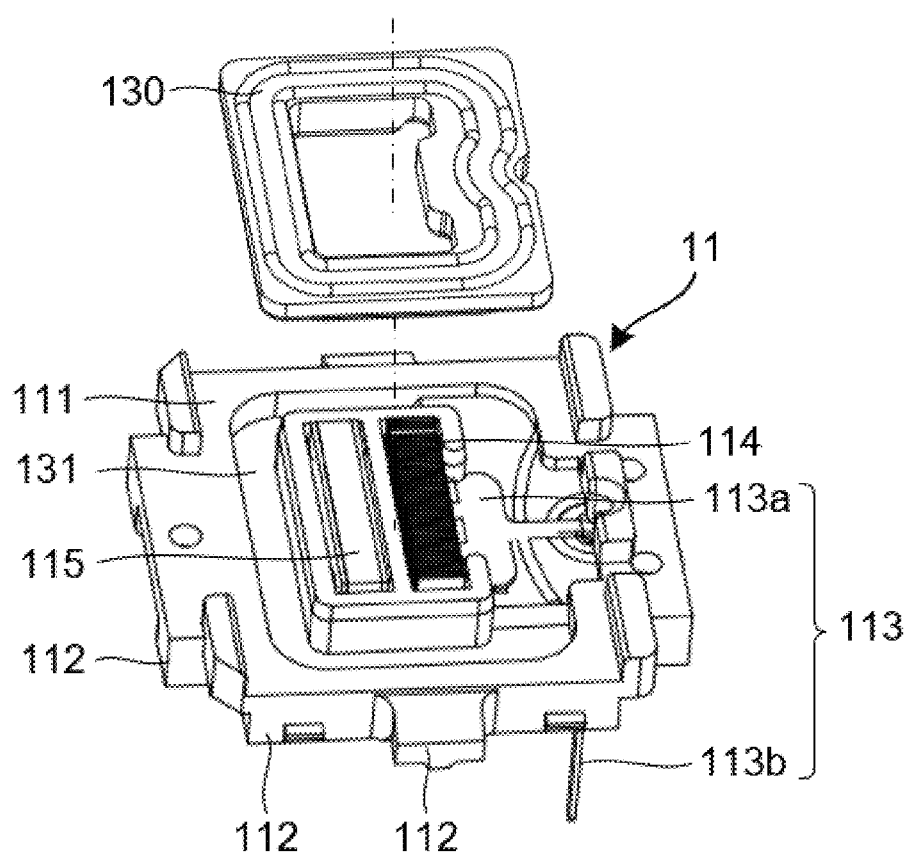
FIG. 2a is a schematic perspective view of the sensor structure and the sealing member according to the embodiment of the present invention.
Figure 2B:
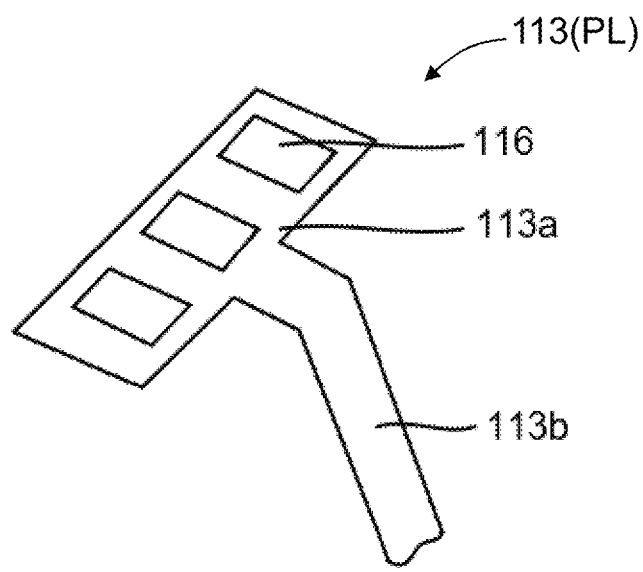
FIG. 2b is a schematic perspective view of the sensor according to an embodiment of the present invention.

FIG. 2a is a schematic perspective view of the sensor structure 11 and the sealing member 130 according to the embodiment of the present invention. FIG. 2b is a schematic perspective view of the sensor 113 according to the embodiment of the present invention.

The sensor structure 11 includes a sensor base 111 and a sensor 113. A second fastener part 112 is provided at the edge of the sensor base 111 for fastening with the first fastener part 102. In the embodiment of the present invention, the contour shape of the edge of the mounting hole 101 matches that of the sensor base 111. Therefore, when the sensor structure 11 and the bottom case 10 are fastened with each other, the edge of the mounting hole 101 and the edge of the sensor base 111 are interlocked with each other, and the sensor base 111 is installed in the mounting hole 101. In addition, since the first fastener part 102 and the second fastener part 112 are both disposed at the edge, the position where these two fastener parts are fastened is not higher than the top of the sensor structure 11. Such a design reduces the height of the sensor structure 11, so that no extra space is required in the transmitter, which reduces the thickness of the transmitter and ultimately reduces the overall volume of the analyte detection system.

Referring to FIG. 2b, the sensor 113 includes a signal output end 113a and a detection end 113b. The signal output end 113a needs to be electrically connected to the second electrical connection areas of the transmitter to output the detection signal to the transmitter. The detection end 113b is used to pierce subcutaneous tissue of a human body to detect body fluid analyte parameters. In the embodiment of the present invention, the signal output end 113a is embedded in the sensor base 111.

The surface of the signal output end 113a is provided with the first electrical connection areas 116 which are insulated from each other. The surface of the sensor 113 is further provided with electrodes and electrode leads (not shown) for detecting parameters of the fluid analyte. The signals of the electrodes need to be derived through the first electrical connection areas 116. Generally, at least two detection electrodes are provided on the sensor 113, so in the present invention, at least two first electrical connection areas 116 are provided on the surface of the signal output end 113a to be electrically connected to different electrodes. As in the embodiment of the present invention, there are three electrodes on the sensor 113, thus the number of the first electrical connection areas 116 is three.

The sealing member 130, which has dust-proof feature, moisture-proof feature, water-proof feature and the like, is configured to seal the connection position between the signal output end 113a and the electrical connection areas.

The sensor base 111 of the embodiment of the present invention is provided with a groove 131 in which the sealing member 130 is placed. The installed sealing member 130 surrounds the connection position between the signal output end 113a and the electrical connection areas to achieve sealing effect.

It should be noted that, in other embodiments of the present invention, when the transmitter is installed, the transmitter and the bottom case 10 form a sealed structure, therefore the sealing member 130 may not be provided.

In the embodiment of the present invention, the first elastic conductive member 114 and the second elastic conductive member 115, which are finally located between the transmitter and sensor structure 11, are further disposed on the top of the sensor base 111. In another embodiment of the present invention, only the first elastic conductive member 114 is disposed, which will be described in detail below.

It should be noted that, in other embodiments of the present invention, the first elastic conductive member 114 and the second elastic conductive member 115 may not be provided, while the corresponding positions of the transmitter and the sensor structure are directly connected with each other.

Figure 3:
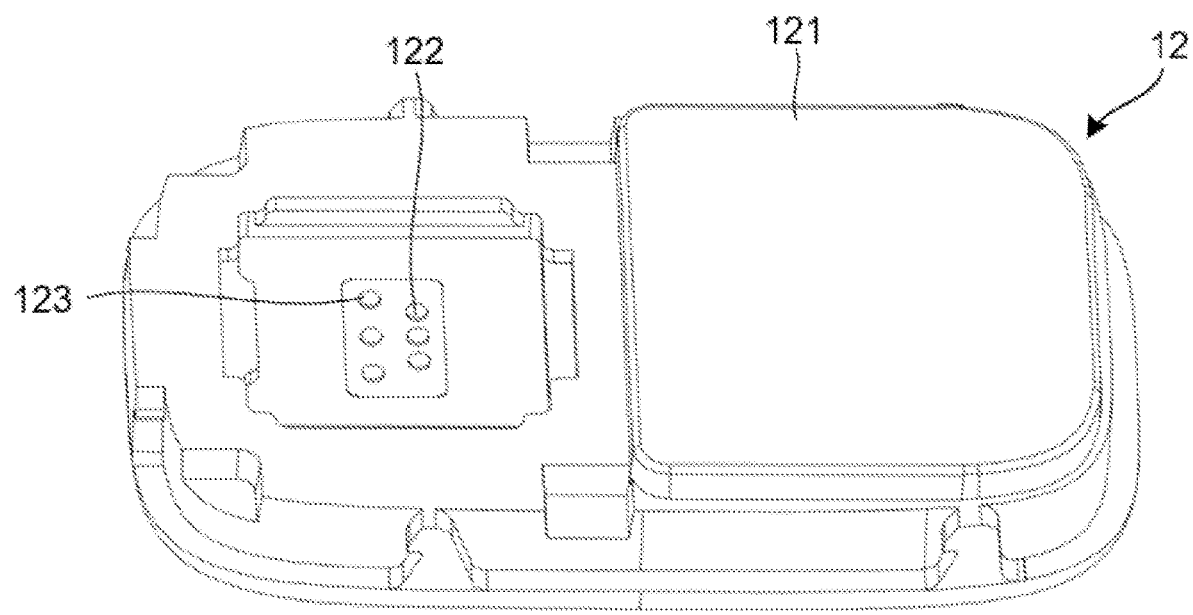
FIG. 3 is a schematic perspective view of the transmitter according to an embodiment of the present invention.

FIG. 3 is a schematic perspective view of the transmitter 12 according to the embodiment of the present invention.

The transmitter 12 is provided with second electrical connection areas 122 which are insulated from each other. In the embodiment of the present invention, the second electrical connection areas 122 are exposed and protrude from the transmitter housing 121 to facilitate electrical connect with the corresponding first electrical connection areas 116. Specifically, in the embodiment of the present invention, the second electrical connection areas 122 are metal contacts which are much smaller, making the internal structure of the analyte detection system much more compact and reducing the overall volume of the analyte detection system.

In another embodiment of the present invention, since the first elastic conductive member 114 is set between the second electrical connection areas 122 and the first electrical connection areas 116, the second electrical connection areas 122 may not protrude from the surface of the transmitter case 121.

In the embodiment of the present invention, the transmitter 12 is further provided with at least two third electrical connection areas 123 which can be configured to activate the analyte detection system or used as an interface to charge the transmitter 12. And the third electrical connection areas 123 will electrically connect with the second elastic conductive member 115. In the embodiment of the present invention, the position and shape of the third electrical connection areas 123 and their position relationship with the second electrical connection areas 122 are not specifically limited.

Since the analyte detection system needs to be activated remotely and does not need to be charged, in another embodiment of the present invention, the third electrical connection areas 123 are not provided. Obviously, there is also no need to provide the second elastic conductive member 115 in the analyte detection system.

Figure 4A:
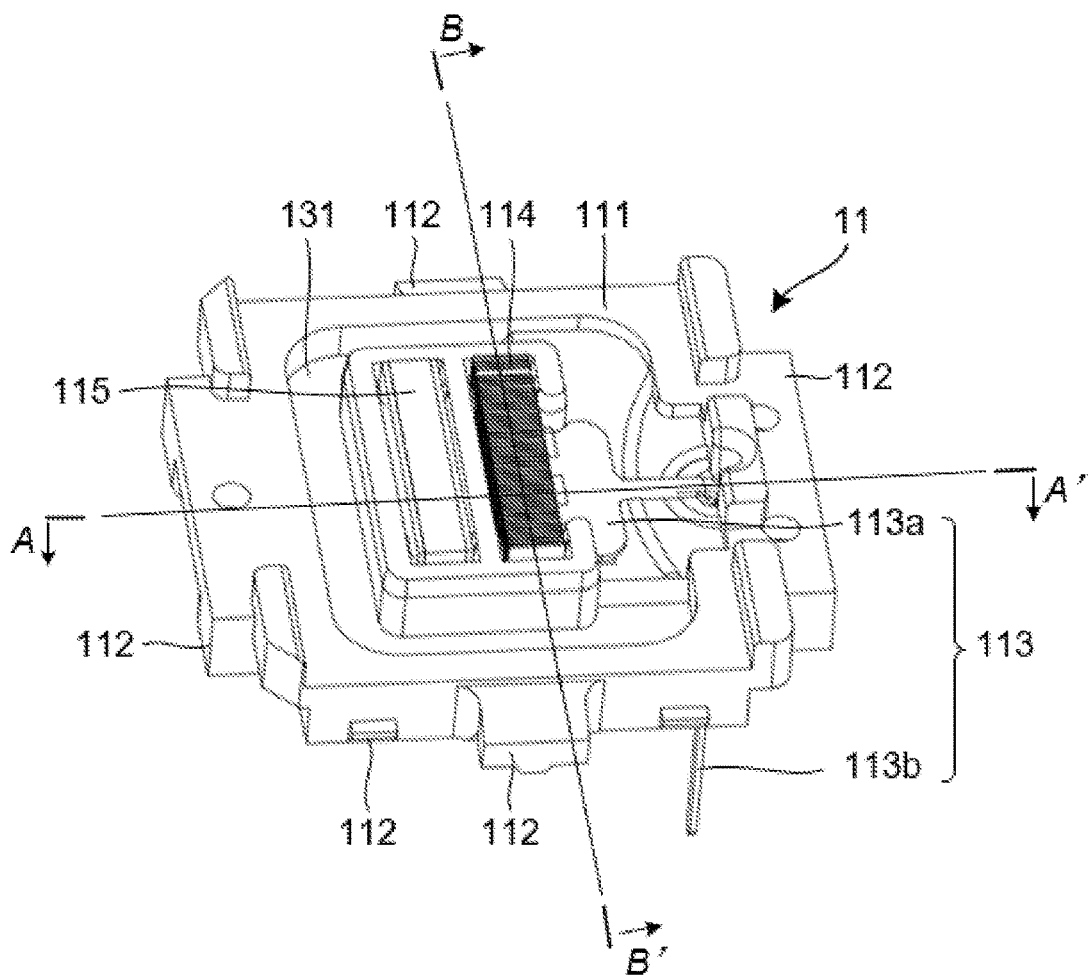
FIG. 4a is a schematic perspective view of the sensor structure according to an embodiment of the present invention.
Figure 4B:
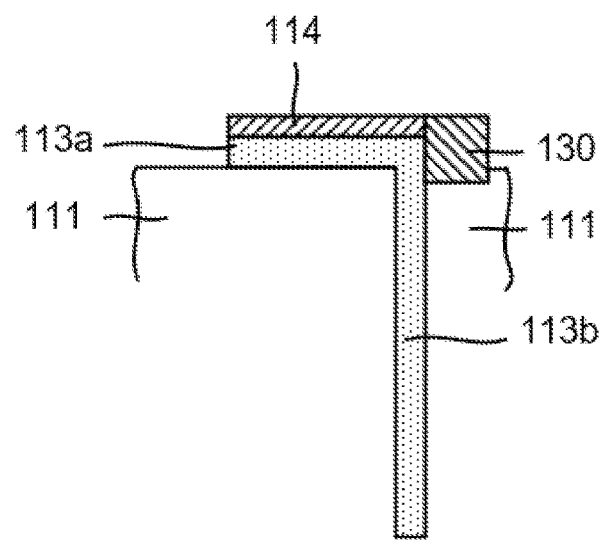
FIG. 4b and FIG. 4c are schematic diagrams of sensors and their adjacent structures of different embodiments obtained along the section line A-A' in FIG. 4a, respectively.
Figure 4C:
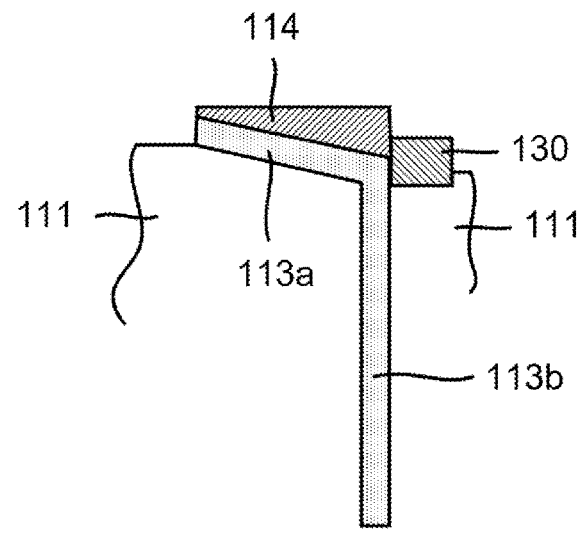
Figure 4D:
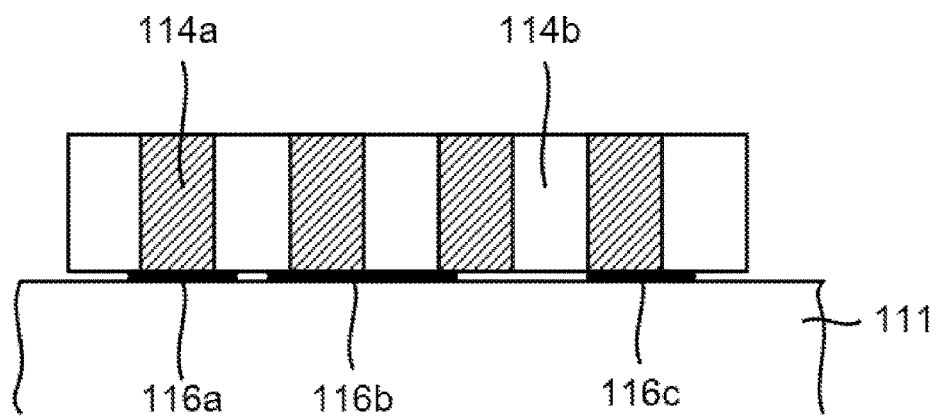
Figure 4E:
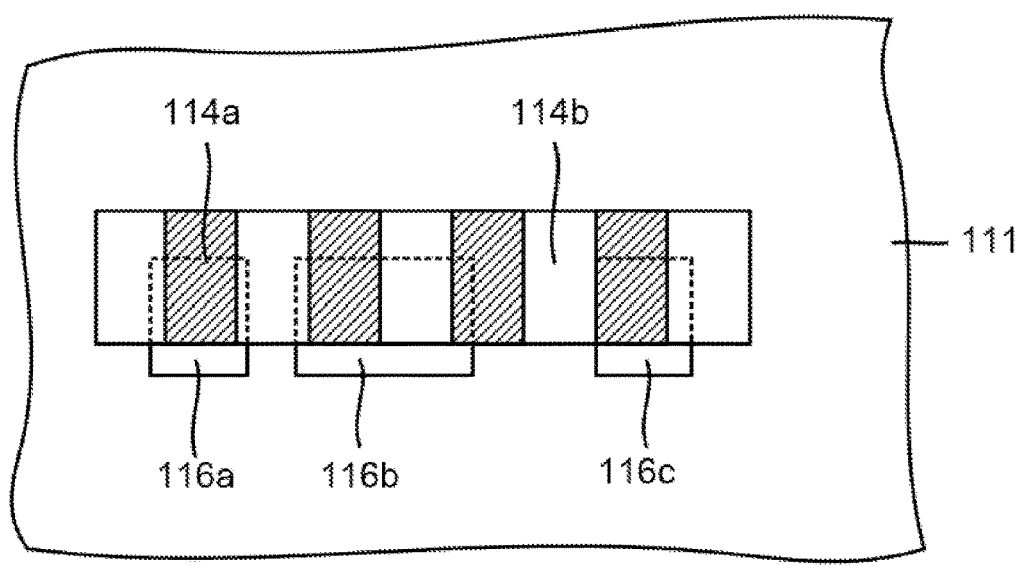
FIG. 4e is a schematic top view of the longitudinal section of FIG. 4d.
Figure 4F:
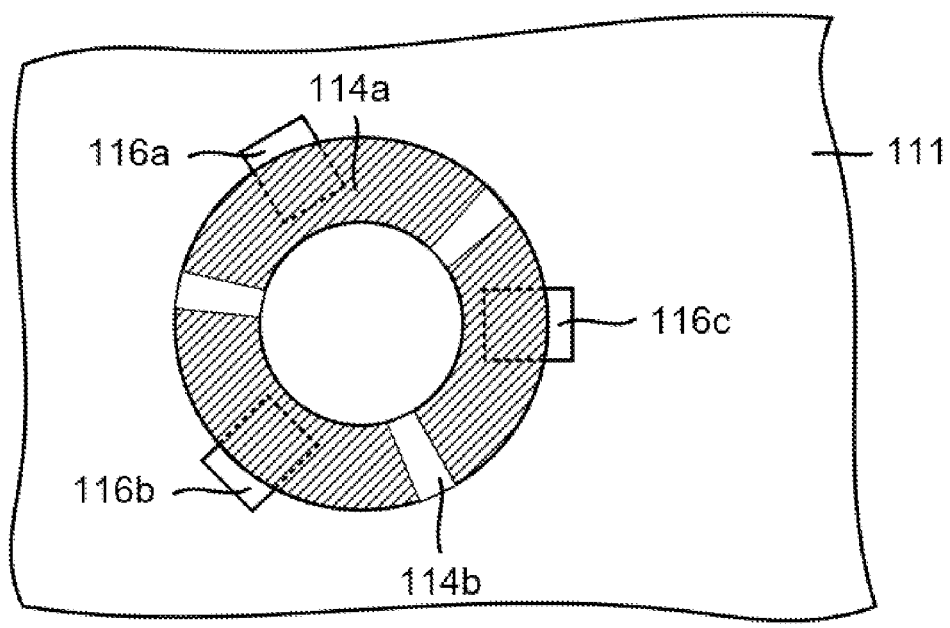
FIG. 4f-FIG. 4h are top views of the first elastic conductive member according to different embodiments.
Figure 4G:
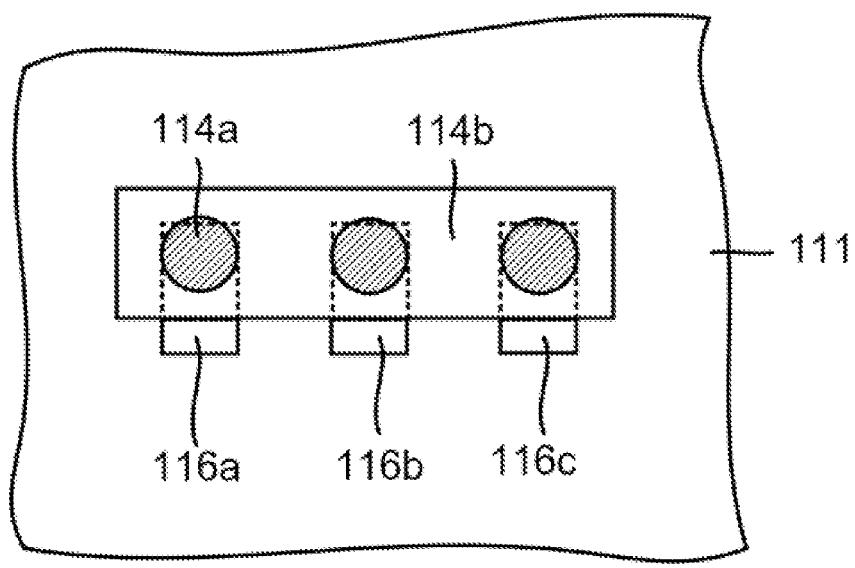
Figure 4H:
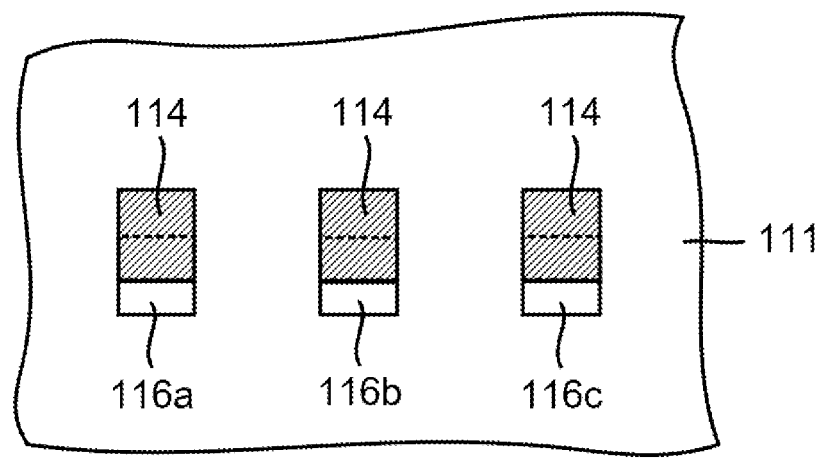
Figure 4I:
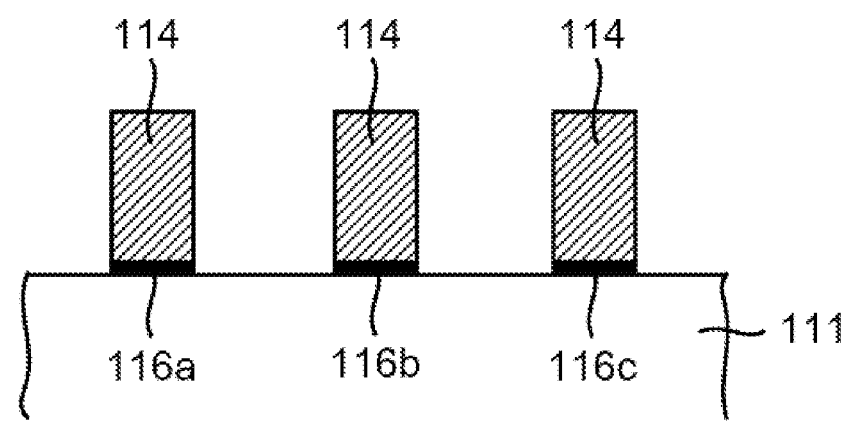
FIG. 4i is a schematic structural view of a longitudinal section of the structure of FIG. 4h.

FIG. 4a is a schematic perspective view of the sensor structure 11. FIG. 4b and FIG. 4c are schematic diagrams of sensors 113 and their adjacent structures of different embodiments obtained along the section line A-A' in FIG. 4a, respectively. FIG. 4d is a schematic cross-sectional structural view of the first elastic conductive member 114 obtained along a section line B-B' in FIG. 4a. FIG. 4e is a schematic top view of the longitudinal section of FIG. 4d. FIG. 4f-FIG. 4h are top views of the first elastic conductive member 114 according to different embodiments. FIG. 4i is a schematic structural view of a longitudinal section of the structure of FIG. 4h.

As shown in FIG. 2b and FIG. 4a, in the embodiment of the present invention, the shape of the sensor 113 is a polyline PL. The signal output end 113a of the sensor 113 is bent toward the top of the sensor base 111. The bent sensor 113 will reduce the entire height of the top of the sensor structure 11, thus, reducing the overall thickness of the analyte detection system and making the structure of the analyte detection system much more compact.

In the embodiment of the present invention, the signal output end 113a has a planar structure. The signal output end 113a is laid on the top of the sensor base 111. At this time, the cross sections of the signal output end 113a and the detection end 113b are perpendicular to each other, as shown in FIG. 4b. For the thickness of the sensor 113 is extremely small (usually at micron level), the top of the sensor 113 is flush with the top surface of the sensor base 111.

As shown in FIG. 4c, in another embodiment of the present invention, the signal output end 113a of the sensor 113 is bent toward the top of the sensor base 111, but the cross section of the signal output end 113a and the detection end 113b are not perpendicular, which also reduces the top height of the sensor structure 11.

In another embodiment of the present invention, the signal output end 113a is curved as a whole in the direction toward the top surface of the sensor base 111, that is, the shape of the sensor 113 is an arc, preventing the sensor 113 from being easily broken.

It should be noted that, in other embodiments of the present invention, the sensor 113 may also have other possible shapes, such as a shape of a polyline with multiple straight or curved lines, which is not specifically limited herein.

As mentioned above, the embodiment of the present invention is further provided with the first elastic conductive member 114. Specifically, the first elastic conductive member 114 is disposed between the first electrical connection areas 116 and the second electrical connection areas 122, so that these two portions have better electrical connection.

In the embodiment of the present invention, the first elastic conductive member 114 includes conductive areas 114a and insulation area 114b. The insulation area 114b is spaced between two adjacent conductive areas 114a, and the conductive areas 114a and the insulation area 114b expand across the first elastic conductive member 114 in the vertical direction shown in FIG. 4d, which ensures that after the first electrical connection areas 116 and the second electrical connection areas 122 are electrically connected. The first elastic conductive member 114 can only conduct electricity in the vertical direction without conducting electricity in the horizontal direction. Such a design achieves electrical conductivity of the first elastic conductive member 114 and also makes the different first electrical connection areas 116 or the different second electrical connection areas 122 insulated.

Please continue to refer to FIG. 4d, after the first elastic conductive member 114 and the first electrical connection areas 116a, 116b, 116c are electrically connected, the insulation area 114b is separated between two adjacent first electrical connection areas 116. The number of separated insulation area 114b between two adjacent first electrical connection areas 116 may be one, multiple, or less than one (as shown between 116a and 116b in FIG. 4d), which is not specifically limit herein.

Specifically, in the embodiment of the present invention, the first elastic conductive member 114 is a conductive rubber strip. The conductive areas 114a and the insulation areas 114b, all penetrating the first elastic conductive members 114, respectively, are disposed alternatively. The top view of the conductive rubber strip is shown in FIG. 4e. In another embodiment of the present invention, according to the position and shape of the first electrical connection areas 116, the shape of the first elastic conductive member 114 is a circular ring in the top view. Conductive areas 114a and insulation areas 114b are disposed in the first elastic conductive member 114 in a circular shape alternatively, whose top structure view is shown in FIG. 4f. In another embodiment of the present invention, the different conductive areas 114a are surrounded by the insulation areas 114b, as the top view of the conductive areas 114a shown in FIG. 4g.

It should be noted that, in other embodiments of the present invention, the whole first elastic conductive member 114 may be electrically conductive, and the plurality of first elastic conductive members 114 are only correspondingly disposed between the first electrical connection areas 116 and the second electrical connection areas 122 with the different first elastic conductive members 114 being separated by a certain distance to achieve insulation, as shown in FIG. 4h and FIG. 4i. Or the first elastic conductive members 114 may be other possible structures, which are not specifically limited herein, as long as the condition for electrically connection between the first electrical connection areas 116 and the second electrical connection areas 122 is satisfied.

Similar to the first elastic conductive member 114, conductive areas (not shown) is also provided in the second elastic conductive member 115. But the difference with the first elastic conductive member 114 is that when the analyte detection system is assembled, the third electrical connection areas 123 and the conductive areas of the second elastic conductive member 115 are electrically connected, achieving the electrical connection between the different third electrical connection areas 123.

Figure 5A:
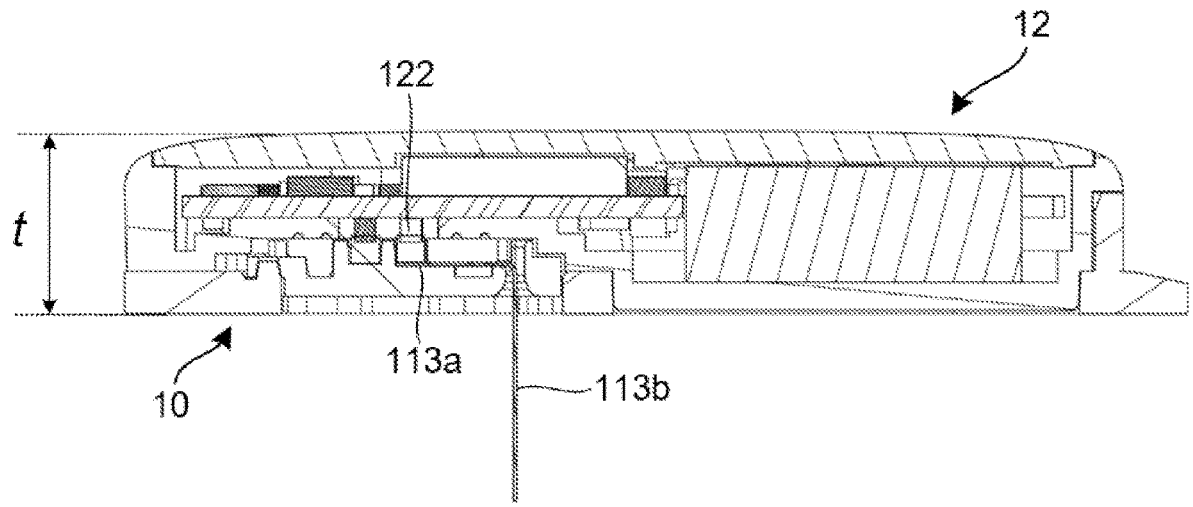
FIG. 5a is a side view of a highly integrated analyte detection system after installation according to an embodiment of the present invention.
Figure 5B:
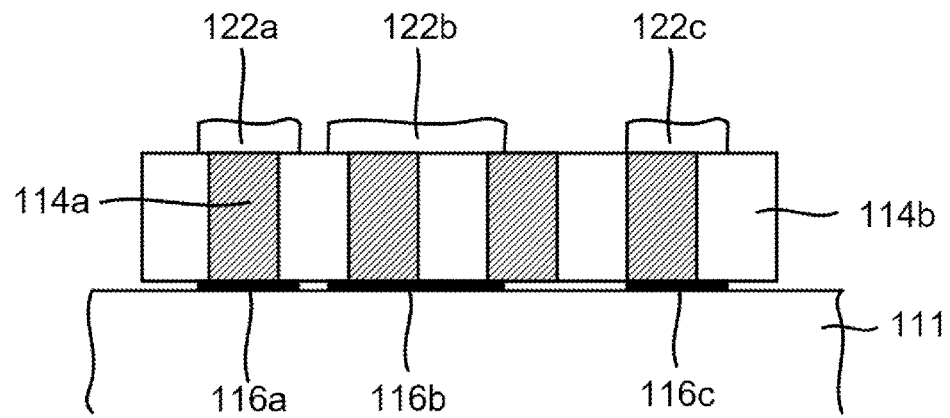
FIG. 5b is a schematic longitudinal cross-sectional structural view of the first electrical connection areas and the second electrical connection areas in FIG. 5a after being electrically connected.
Figure 5C:
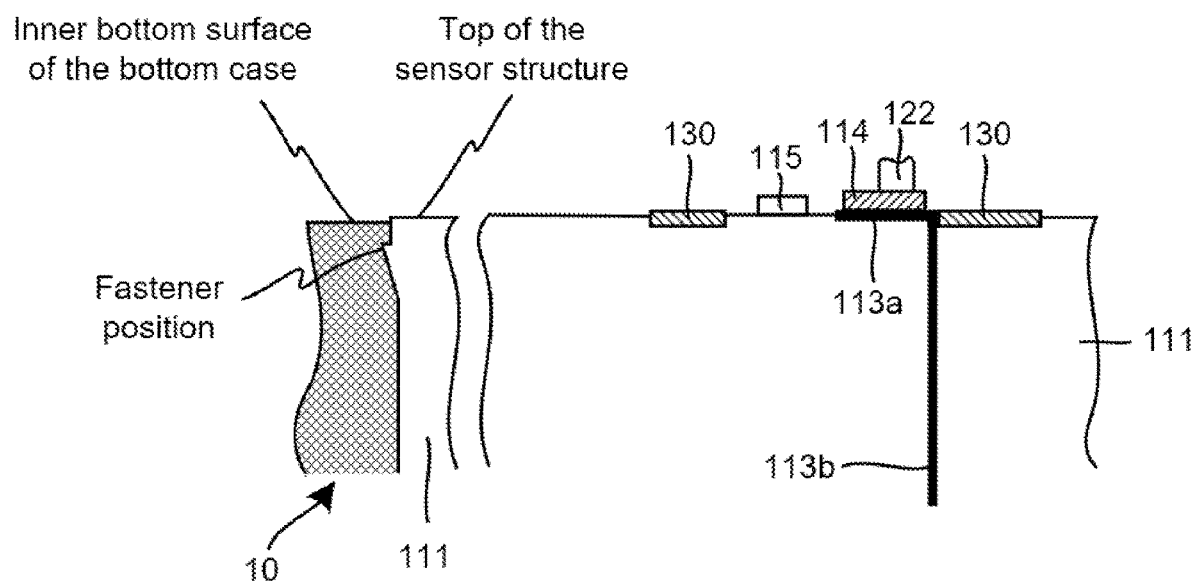

FIG. 5a is a side view of a highly integrated analyte detection system after installation according to an embodiment of the present invention. FIG. 5b is a schematic longitudinal cross-sectional structural view of the first electrical connection areas 116 and the second electrical connection areas 122 in FIG. 5a after being electrically connected. FIG. 5c is a longitudinal sectional structural view of the highly integrated analyte detection system of FIG. 5a.

As shown in FIG. 5b, the number and position of the second electrical connection areas 122 and the first electrical connection areas 116 correspond to each other. Obviously, conductive area(s) 114a must be provided between each of the first electrical connection areas 116 and the corresponding second electrical connection areas 122, making these two portions achieve electrical connection. Therefore, the number of the insulation areas 114b between the adjacent second electrical connection areas 122 is the same as that of the first electrical connection areas 116, as described above.

In the existing body fluid detection device, the whole sensor is perpendicular to the skin surface at the puncture position, or the fastener position between the sensor structure and the bottom case is higher than the inner bottom surface of the bottom case. The distance between the top of the sensor structure and the inner bottom surface of the bottom case includes not only the height of the fastener position but also the length of the signal output end. Extra space must be required to accommodate these portions protruding from the bottom board of the bottom case, resulting in thicker analyte detection system and poorer user experience.

Compared with the existing body fluid detection device, in the embodiment of the present invention shown in FIG. 5c, the signal output end 113a of the sensor 113 has a shape of a polyline or an arc toward the top surface of the sensor base 111, and the top of the sensor structure 11 is not higher or slightly higher than the inner bottom surface of the bottom case 10. As in the embodiment of the present invention, the height of the top of the sensor structure 11 protruding from the inner bottom surface of the bottom case 10 is less than or equal to 0.8 mm. At the same time, the fastener position of the sensor base 111 and the bottom case 10 is not higher than the top of the sensor structure 11. If the overall thickness of the analyte detection device is t, compared with the existing detection device, the thickness t of the analyte detection device in the embodiment of the present invention will be reduced by more than 35%, as shown in FIG. 5a. Therefore, no extra space is required on the transmitter 12, reducing the thickness of the transmitter 12 and making the structure of the analyte detection system more compact, furthermore, as a result, reducing the volume of the analyte detection system and greatly enhancing the user experience.

In summary, the present invention discloses a highly integrated analyte detection system in which the signal output end is a polyline or an arc toward the top surface of the sensor base, reducing the height of the sensor structure and making the structure of the analyte detection system more compact, furthermore, as a result, reducing the volume of the analyte detection system and greatly enhancing the user experience.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. An integrated analyte detection system, including:
   a bottom case;
   a sensor structure, the sensor structure and the bottom case are fastened with each other, the sensor structure includes a sensor and a sensor base, the sensor includes a signal output end and a detection end, the signal output end has a shape of a polyline or an arc toward a top surface of the sensor base, and at least two first electrical connection areas insulated from each other are provided on a surface of the signal output end; and
   a transmitter, the transmitter and the bottom case are fastened with each other, and the transmitter is provided with second electrical connection areas, which are insulated from each other, corresponding to the at least two first electrical connection areas, each second electrical connection area is electrically connected to a corresponding first electrical connection area, wherein a mounting hole is provided on a bottom board of the bottom case, a first fastener part is provided at an edge of the mounting hole, and a second fastener part is provided at an edge of the sensor base, contour shapes of the edge of the sensor base and that of the mounting hole match each other, the first fastener part and the second fastener part are fastened with each other, and the edge of the mounting hole and the edge of the sensor base are interlocked, so that the sensor base is installed and fixed in the mounting hole.

2. The integrated analyte detection system of claim 1, wherein,
   the second electrical connection areas are metal contacts.

3. The integrated analyte detection system of claim 1, wherein,
   the signal output end is a planar structure and is laid on a top of the sensor base.

4. The integrated analyte detection system of claim 1, further including a sealing member, the sealing member is arranged around a position where the signal output end is electrically connected with the second electrical connection areas.

5. The integrated analyte detection system of claim 1, further including a first elastic conductive member disposed between the at least two first electrical connection areas and the second electrical connection areas.

6. The integrated analyte detection system of claim 5, wherein,
   the first elastic conductive member includes conductive areas and insulation areas, and one insulation area is spaced between every two adjacent conductive areas, the conductive areas and the insulation areas expand across the first elastic conductive member in a vertical direction, respectively.

7. The integrated analyte detection system of claim 6, wherein,
   the conductive areas and the insulation areas are separated from each other, the at least two first electrical connection areas are electrically connected with corresponding second electrical connection areas through the conductive areas, and one insulation area is disposed between every two adjacent first electrical connection areas or every two adjacent second electrical connection areas.

8. The integrated analyte detection system of claim 6, wherein,
   the transmitter is provided with at least two third electrical connection areas, and a second elastic conductive member is disposed between the third electrical connection areas and the sensor base, after electrical connecting with the second elastic conductive member, the different third electrical connection areas are connected.

* * * * *